Figure 1:
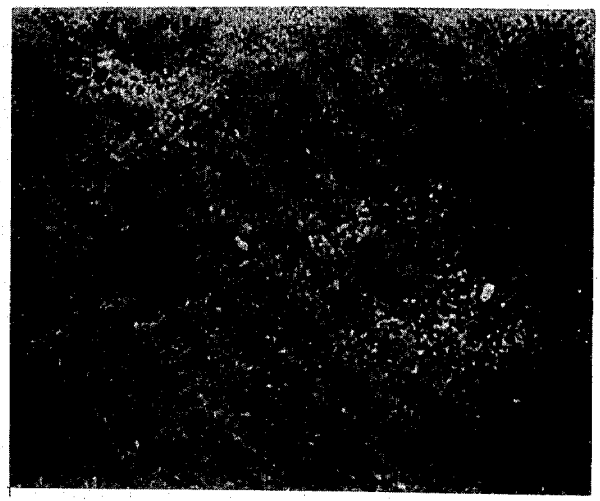

United States Patent [19]

Koshugi

[11] 4,336,070
[45] Jun. 22, 1982

[54] PROCESS FOR PREPARING POROUS SHAPED MATERIAL OF ACYLATED CHITIN DERIVATIVE

[75] Inventor: Junichi Koshugi, Tokyo, Japan

[73] Assignee: Kureha Kagaku Kogyo Kabushiki Kaisha, Tokyo, Japan

[21] Appl. No.: 168,315

[22] Filed: Jul. 10, 1980

[30] Foreign Application Priority Data

Jul. 20, 1979 [JP] Japan ................................ 54-92898

[51] Int. Cl.$^3$ ............................................. C08B 37/08
[52] U.S. Cl. .................................. 106/122; 106/162; 536/20
[58] Field of Search .................. 106/122, 163; 536/20; 106/162

[56] References Cited

U.S. PATENT DOCUMENTS 3,953,608  4/1976  Vanlerberghe ....................... 536/20
4,111,810  9/1978  Arai et al. ............................ 210/23

FOREIGN PATENT DOCUMENTS 13181   9/1980  European Pat. Off. .............. 536/20
565343  11/1944  United Kingdom .

OTHER PUBLICATIONS

Chem. Abst. 82: No. 46, Jun. 30, 1975, p. 122, 173038t.
Riccard A. A. Muzzarelli, "Modified Chitosan and Their Chromatrographic Performances", Proceedings of Int. Conference on Chitin/Chitosan, held in Boston, May 78, pp. 335-347.

Primary Examiner—Theodore Morris
Attorney, Agent, or Firm—Wegner & Bretschneider

[57] ABSTRACT

A process for producing a porous shaped material of acylated chitin derivative wherein a soluble derivative of chitin is acylated, characterized in that an aqueous solution of the derivative of chitin containing a diluent, a porosity-regulating agent and a surfactant is added into a solution of an organic acid anhydride containing a surfactant.

9 Claims, 4 Drawing Figures

X2800

X2800

X1400

X1400

X3000

PROCESS FOR PREPARING POROUS SHAPED MATERIAL OF ACYLATED CHITIN DERIVATIVE

This invention relates to a novel process for preparing a porous shaped material of acylated chitin derivative, the material being useful as fillers for chromatographic columns, a base material for immobilizing enzymes and so on.

Chitin is a mucopolysaccharide of poly-N-acetyl-D-glucosamine, and its amount in nature compares favorably with that of cellulose in nature. However, since the chitin is a highly crystalline substance and the intermolecular bonding thereof by its aminoacetyl groups is extremely stable, it is very much difficult to find out an appropriate solvent to dissolve, disperse or swell the chitin favorably. Accordingly, the development pertaining to the utilization of chitin resources is far behind that of cellulose and other polysaccharides.

In these situations, the inventor of the present invention has previously offered a method for preparing a soluble derivative of chitin by carboxylalkylating the hydroxyl group of chitin and then by de-acetylating the thus formed carboxylalkylated chitin (refer to the Japanese Patent Application No. 161,391/1978) and a shaped material of acylated chitin derivative obtained by acylating the above-mentioned soluble derivative of chitin with an organic acid anhydride (refer to the Japanese patent application No. 161,388/1978). The obtained shaped material may have its outer surface comprising chemically stable chitin or N-acylated chitosan and its internal part constituted of the amphoteric and polymeric electrolyte of the de-N-acetylated carboxyalkylchitin. Particularly, the above-mentioned shaped material of the acylated chitin derivative is stable chemically and in living bodies and safe from the biological view points, and moreover, it has cationic and anionic groups in the internal part thereof. Accordingly, its utilization for use, for instance, in blood perfusion and in an adsorbent which is orally administrated to adsorb and remove toxins within the gastro-intestinal tracts is expected.

However, the above-mentioned shaped material has a small permissibility to the substances having a molecular weight of more than 70,000 and cannot effectively adsorb the substances having a molecular weight larger than 70,000 or separate them. In other words, the above-mentioned shaped material of acylated chitin derivative is poor in the molecular sieve effectiveness to molecules having molecular weight in a broad range and accordingly, it is insufficient as an adsorbing and separating material for macromolecules such as protein, enzymes, etc. In addition, even if the above-mentioned material possibly adsorb and separate the above-mentioned macromolecules, a defect of the material, that is, the insufficientness in strength has been found in the above-mentioned shaped material of acylated chitin derivative.

The present invention is a result of the further development of the above-mentioned patent applications, and the invention has a main object to provide a novel process for preparing a porous shaped material of acylated chitin derivative which has a favorable ability of molecular sieve and a uniformly and optionally adjustable pore-size, and is excellent in performance and strength.

The present invention provides a process for preparing a porous shaped material of acylated chitin derivative wherein the soluble derivative of chitin is acylated, characterised in that the liquid mixture of an aqueous solution of the soluble derivative of chitin with a diluent, an agent for regulating the porosity of the porous shaped material (hereinafter referred to as a porosity-regulating agent), which comprises a volatile alkylbenzene, and a surfactant is added into an acylating agent containing a surfactant, and if necessary, a further treatment for cross-linking is carried out on the thus acylated product.

The followings are the detailed description of the present invention.

The soluble derivative of chitin according to the invention is defined by a derivative of thitin which is soluble in water or an aqueous dilute acidic solvent such as an aqueous dilute solution of acetic acid, hydrochloric acid, etc. For instance, the soluble derivative of chitin is a compound represented by the following formula:

$$[C_6H_8O_3 \cdot (NH_2)_x \cdot (NHCOCH_3)_y \cdot (OR)_a \cdot (OH)_b]_n$$

wherein R represents a carboxyalkyl group with two to four carbon atoms, a hydroxyethyl group, a hydroxypropyl group, a dihydroxypropyl group or an alkyl group with one to three carbon atoms;

x is a number of 0.1 to 1.0; $y = 1.0 - x$; a is a number of 0 to 1.0 and $b = 1.0 - a$, or a salt thereof. The salt includes an alkali metal salt, an alkaline earth metal salt or an ammonium salt.

The de-N-acetylated products of carboxyalkyl chitin, hydroxyethyl chitin, hydroxypropyl chitin and dihydroxypropyl chitin in the above-mentioned formula have a degree of substitution (a) of preferably 0.1 to 1.0, more preferably 0.3 to 1.0 per one pyranose ring and a degree of de-N-acetylation (x) of 0.1 to 1.0, preferably 0.2 to 0.6 from the view of the solubility to the aqueous solvent and the viscosity of the obtained solution. From the same view, the de-N-acetylated products of alkylchitin in the above-mentioned formula have the degree of substitution (a) of preferably 0.1 to 1.0 and the degree of de-N-acetylation preferably 0.5 to 1.0, and further the de-N-acetylation product of chitin of which a is 0 in the above-mentioned formula has the degree of de-N-acetylation (x) of preferably 0.5 to 1.0.

The above-mentioned liquid mixture is prepared by adding 0.1 to 5 parts by weight of the diluent, 0.001 to 1 part by weight of the porosity-regulating agent and 0.001 to 0.1 parts by weight of the surfactant to one part by weight of the aqueous solution of the derivative of chitin. The order of the above-mentioned addition and its method are not specifically restricted but may be carried out optionally. In usual cases, the diluent was at first added to the aqueous solution of the derivative of chitin to obtain an homogeneous solution, and then the porosity-regulating agent containing the surfactant is added to the homogeneous solution. The thus obtained liquid mixture is usually in a state of emulsified dispersion, however, it may take an appearance of a homogeneous solution according to the proportional amount of the composition therein.

The concentration of the soluble derivative of chitin in the aqueous solution is the larger, the more firm and denser shaped material is obtained, however, it may be usually 0.1 to 10% by weight.

The diluent according to the invention should have a compatibility to the aqueous solution of the derivative of chitin and the porosity-regulating agent. The diluent is used to adjust the viscosity of the liquid mixture and to assist the homogeneous dispersibility of the liquid mixture. Accordingly, when a shaped material is prepared without using the diluent, the pores in the thus prepared shaped material are irregular in size and the shaped material is weak in strength.

As the diluent, alcohols with carbon atoms of one to four, pyridine or compounds represented by the general formula of $R-O\text{-}[(CH_2)_2O]_{\overline{n}}R'$ wherein R and R' represent respectively either a hydrogen atom or an alkyl group of $C_1$ to $C_4$ and n is an integer of 1 to 3 may be mentioned. The diluent is typically exemplified by a compound selected from the group consisting of methanol, ethanol, n-propanol, iso-propanol, pyridine, ethylene glycol, ethylene glycol monomethyl ether, ethylene glycol monoethyl ether, ethylene glycol mono-n-butyl ether, ethylene glycol dimethyl ether, ethylene glycol diethyl ether, ethylene glycol di-n-butyl ether, diethylene glycol monomethyl ether, diethylene glycol monoethyl ether, diethylene glycol mono-n-butyl ether, diethylene glycol dimethyl ether, diethylene glycol diethyl ether and diethylene glycol di-n-butyl ether or mixtures comprising more than two of them.

The porosity-regulating agent according to the invention is significant and used for the object of obtaining a homogeneous acylation into within the shaped material on the acylation of the above-mentioned liquid mixture, which will be described later, and of making the thus obtained shaped material of denatured chitin to be highly strong and highly porous. For those purposes, the porosity-regulating agent of the present invention should be insoluble into water, be inert to the acylating agent and be compatible to the acylating agent and to the diluent, and it is possibly exemplified by the volatile alkylbenzene such as benzene, toluene, xylene, etc. In addition, the amount of addition of the porosity-regulating agent may be optionally determined depending upon the desired pore-size or pore-volume of the shaped material.

The surfactant for use in the process of the invention is preferably non-ionic in nature, for instance, monolaurate, monopalmitate, monostearate, monooleate or trioleate, etc. of sorbitan or polyoxyethylene sorbitan. The above-mentioned surfactant is effective in dissolving or finely dispersing the above-mentioned diluent and the above-mentioned porosity-regulating agent into the aqueous solution of the above-mentioned derivative of chitin and it is further effective in dispersing fibrous material formed by diluting the derivative of chitin with a large amount of the diluent.

The porous shaped material of acylated chitin derivative according to the invention is easily available by treating the above-mentioned liquid mixture with the acylating agent including the surfactant. Particularly, by using an anhydride of an organic acid or a mixture of the anhydride and the organic acid as the acylating agent, the porous shaped material according to the invention is extremely easily obtained in a short time period.

As the organic acid and the acid anhydride, aliphatic and aromatic organic acids with two to twenty carbon atoms and their anhydride may be mentioned. For instance, acetic acid, propionic acid, butylic acid, valeric acid, etc. and their anhydrides are suitable. These acids and acid anhydrides are used singly or in a mixture of more than two of them. The organic acid anhydride may be used without dilution, or used after dilution with a solvent inert to the organic acid or its anhydride, for instance, an organic solvent such as benzene, toluene, xylene, etc. to adjust the rate of acylating reaction and to make the after-treatment of the acylated product easy.

The acylation is carried out at a temperature of 5° to 80° C., preferably 5° to 60° C., however, in the case where the derivative of chitin has the degree of de-N-acetylation of over 0.6, a higher temperature is preferable. In addition, the acylated product of the derivative of chitin is either chitin, o-acylated chitin, N-acylated chitosan, or a mixture thereof.

In the next place, the mode of adding the above-mentioned liquid mixture into the acylating agent can be suitably selected according to the use and form of the porous and shaped material of the present invention.

For instance, a mode can be exemplified in which the liquid mixture prepared as mentioned above is dropped into an organic acid anhydride containing the surfactant under agitation to form dispersed small particles.

The amount of the organic acid anhydride used as the acylating agent is not particularly restricted, however, in general, it may be 1 to 100 times by equivalent, preferably 5 to 20 times by equivalent per one equivalent of amino group of the de-N-acetylated product of chitin or chitin derivative according to the invention. And, in order to regulate the dispersed state of the particles of the liquid mixture in the organic acid anhydride, it is preferable to add an amount of the organic solvent 10 to 1,000 times by weight, preferably 10 to 500 times by weight of the liquid mixture to the above-mentioned acylating agent.

The amount of addition of the surfactant to the acylating agent is not particularly restricted and, in usual, it may be selected from the range of 0.01 to 0.1 parts by weight to one part by weight of the liquid mixture. In addition, the dispersing and formulating machine for use in dispersing and shaping the material of acylated chitin derivative of the present invention may be chosen from a stirrer provided with usual stirring blades, static mixer, homogenizer or the like.

As has been described, in the above-mentioned mode, the reaction proceeds instantaneously from the surface of the droplets of the above-mentioned aqueous solution to form a insoluble membrane made of acylated product of derivative of chitin with the result of producing capsule-like product of spherical shape. And on the continuation of the above-mentioned reaction, the organic acid anhydride diffuses into within the droplet to form a gel optionally insolubilized. After carrying out the reaction for a predetermined time period, gel-like porous spherical particles comprising acylated chitin derivative of the present invention are obtained by separating the particles and washing the particles to remove the unreacted organic acid anhydride from the particles. The thus obtainable spherical particles may have a diameter ranging from about 1 to 10,000 microns according to the dispersing degree, the viscosity of the liquid mixture, etc.

In order to change the compactness of the gel-like porous material of the invention, the concentration of the derivative of chitin in the aqueous solution, the temperature and the time period of the reaction, the amount of the diluent, etc. are changed. According to the invention, the compactness will be changed to be such that the threshold molecular weight of the substance passable through the pores of the product of the present invention is in the range of 500 to 400,000.

In addition, minute spherical particles of porous gel comprising the material of acylated product of the present invention can be prepared by at first spraying an aqueous solution of the derivative of chitin into a gaseous phase of the organic acid anhydride to instantly acylate the surfacial layer of the particle to form a insoluble membrane and then by bringing the particles into reaction in the solution containing the acylating agent.

As another mode, the spinning of the liquid mixture through nozzles into a liquid containing the organic acid anhydride is exemplified. In this mode, a fiber-shaped material at least the surface layer of which is insolubilized is obtained. By washing the fiber-shaped material, gel-like porous and fiber-shaped material according to the invention is possibly available. Or, by using slit-formed nozzles, gel-like porous and film-shaped material comprising acylated product according to the present invention is obtained. In both cases of film-shaped material and of fiber-shaped material, it is also possible to obtain hollow-shaped material, and to control the thickness and the compactness of the membrane according to the necessity as in the case of spherical particles.

Not only restricted to the above-mentioned modes, it is natural that various modes of adding the aqueous solution of the derivative of chitin into the acylating solution can be taken.

The gel-like and porous shaped material according to the present invention obtainable by the above-mentioned methods has its broad water-content ranging 10 to 100 times by weight of the weight of the material in a dry state.

The porous and shaped material according to the present invention can be subjected to cross-linking according to the necessity, and the cross-linking can be carried out, for instance, by the following method:

At first, the water content of the gel-like porous and shaped material of the invention is reduced to 2 to 3 times by weight of the weight of the material in a dry state by a treatment such as centrifugation, etc., and then the gel-like material is immersed into an aqueous solution of sodium hydroxide (concentration of larger than 40% by weight) in an amount of more than 2 times, preferably 4 to 30 times by weight of the weight of the material in dry state. The immersion is carried out at a temperature of lower than 15° C. for 1 to 5 hours. After the immersion is over, the excess solution of sodium hydroxide is removed off while maintaining the state of immersion in an aqueous solution of sodium hydroxide in an amount of 3 to 6 times by weight of the weight of the material in dry state. Then the mixture is left at a temperature of 10° to 0° C. for one to 24 hours to obtain a pre-treated material by alkali. In addition, it is preferable for the next step of cross-linking to subject the immersed material to freezing at a temperature of 0° to −30° C. for one to 24 hours. Then, the above-mentioned pre-treated material by alkali is dispersed into water or an organic solvent containing a cross-linking agent in the amount of 0.1 to 3 times, preferably 0.5 to 2 times by mol per one pyranose ring of the acylated product to react for 5 to 48 hours at a temperature of lower than 15° C. After the reaction is over, the reaction product is washed with water and is neutralized to be the water-insoluble porous and shaped material.

As the cross-linking agent, an epoxy-type compound such as epichlorohydrin, epibromohydrin, 2,3-dibromopropanol and 2,3-dichloropropanol is suitable. In addition, the degree of cross-linking may be 0.01 to 0.3 per one unit of pyranose ring determined by elementary analytical values.

As has been shown in the above-mentioned explanation, according to the invention, it is easily possible to prepare the optionally shaped material such as spherical, fiber-like, film-like, etc. As the shaped material of the invention is constituted of acylated product of soluble derivative of chitin, which is porous, permeable, stable chemically and in living bodies and safe, it is applicable to a broad range of uses.

Particularly, the spherically shaped material of the present invention is utilizable as an ion-exchanger by leaving some amino groups intact with the controlled amount of acylating agent.

Since the material according to the present invention is extremely stable and safe to living bodies, it is utilizable in the field concerning living bodies, for instance, in blood perfusion, as an adsorbent orally administered to adsorb toxins within the gastro-intestinal tracts or a coating material for adsorbents, etc. In addition, in the case of using the material in contact with the blood, there is a method in which some amino groups of the material are left free to form polyions with an antithrombogenic substance such as heparin, chitosan sulfate, chitin sulfate, etc., and more preferably, the amino groups are sulfated.

As has been described above, the present invention is epoch-making in effective utilization of chitin which has hitherto been a resource with limited usage, and innumerable developments are expected as to its usage.

The present invention will be explained more in detail while referring to the following unlimited examples:

EXAMPLE 1

Into 200 g of an aqueous 2% solution of acetic acid, 5 g of a de-N-acetylated product (degree of de-N-acetylation of 0.9) of chitin were dissolved. A liquid mixture prepared by dissolving 3 g of sorbitan monooleate as the surfactant and 20 g of toluene as the porosity-regulating agent into 100 g of ethanol as the diluent was added to the above-mentioned aqueous solution under agitation to emulsify the solution. On the other hand, 30 g of polyoxyethylene sorbitan monooleate and 50 g of acetic anhydride were dissolved in 3 liters of toluene in a vessel provided with a bow-type stirrer, and then the above-mentioned emulsified liquid containing de-N-acetylated chitin was added into the vessel under agitation at 1,000 rpm at room temperature to make a dispersion in which a reaction took place.

After reacting for one hour, 2 liters of ethanol was added to the dispersion under agitation to obtain a transparent spherically shaped material.

After separating the material by filtration and washing the separated material repeatedly with ethanol, the washed material was dispersed into distilled water and it was neutralized by an aqueous 1 N solution of sodium hydroxide. After filtration and repeated washing with water, a gel-like porous and shaped material of 50 to 150 microns in diameter under a microscope was obtained.

The thus obtained product contained 20 g of water per one gram of the dry matter. The elementary analytical composition of the dried specimen of the product was as follows:

Carbon: 46.5%, Hydrogen: 6.8%, Oxygen: 40.3% and Nitrogen: 6.7%.

The above-mentioned analytical data coincided well with those of chitin. In the infrared absorption spectrum of the dried specimen, the band of an amino group appearing at 1500 to 1530 cm$^{-1}$ could not be detected, suggesting the conversion of the amino group to the aminoacetyl group.

In addition, the dried specimen of the thus obtained product did not dissolved in an aqueous 5% solution of acetic acid.

EXAMPLE 2

Into 150 g of an aqueous 2% solution of acetic acid, 10 g of de-N-acetylated product of hydroxyethyl chitin (degree of hydroxyethylation of 1.0 and degree of de-N-acetylation of 0.6) were dissolved. A liquid mixture prepared by dissolving 3 g of polyoxyethylene sorbitan monooleate as the surfactant and 10 g of xylene as the porosity-regulating agent into 50 g of ethyleneglycol monomethyl ether as the diluent was added to the above-mentioned aqueous solution under agitation to make an emulsion. This emulsion was added to a solution prepared by dissolving 25 g of polyoxyethylene trioleate and 100 g of propionic anhydride into 5 liters of xylene within a Henschel mixer kept at a temperature of 20° to 25° C., under agitation of 5,000 rpm at room temperature to carry out a reaction in a dispersed state.

After reacting for one hour, 3 liters of ethanol were added to the reaction mixture under agitation of 1,000 rpm to stop the reaction. The product was treated with the same procedures as in Example 1 to obtain a spherically shaped gel-like material of a diameter of 10 to 100 microns under a microscope. The water content of the gel-like material was 10 g per one gram of the dried matter. The elementary analytical composition of the dried matter was: 50.5% of carbon, 6.7% of hydrogen, 36.4% of oxygen and 6.4% of nitrogen.

EXAMPLE 3

Into 180 g of water, 20 g of sodium salt of de-N-acetylated carboxymethylchitin (degree of carboxymethylation of 0.5 and degree of de-N-acetylation of 0.25%) were dissolved. A liquid mixture prepared by dissolving 2 g of polyoxyethylene trioleate as the surfactant and 10 g of toluene as the porosity-regulating agent into a mixed solvent consisting of 20 g of ethylene glycol dimethyl ether and 10 g of pyridine as the diluents was added to the above-mentioned aqueous solution under agitation, and the whole mixture was subjected to de-airing to be the starting material for spinning.

The fibrous shaped material of acylated chitin derivative was obtained by spinning the starting material with using a spinning apparatus which was provided with a tank for the starting material, a reacting vessel of 50 mm in diameter and 5,000 mm in length provided with 25 nozzle-holes of 0.05 mm in diameter, a roller, a solvent-removing vessel containing a mixture of ethanol and water, an another solvent-removing vessel containing hot water at a temperature of 100° C. and a take-up winder. The composition of the solution introduced into the reacting vessel kept at a temperature of 50° C. was as follows:

toluene:acetic anhydride:polyoxyethylene monooleate = 10:5:1 (by weight). The spinning was carried out at an output pressure of 1 kg/cm$^2$.

The thus obtained fibrous material had a diameter of 15 microns in the dry state and 50 microns after immersing into water.

EXAMPLE 4

The gel-like product obtained in Example 2 was dehydrated by centrifugation to the degree of its water-content of 2 ml per one gram of dry matter, and then the thus dehydrated gel was immersed into 23 times by weight of an aqueous 43.5% solution of sodium hydroxide. After compressing the thus immersed gel to remove the aqueous solution of the alkali to the extent of the water content of 3 times by weight of the dry matter and leaving to stand at a temperature of 0° C. for 2 hours, the thus treated gel was frozen at a temperature of −20° C. for one hour.

A solution of epichlorhydrine in amount of 2 times by mol of the above-mentioned gel-like product in dry state in isopropyl alcohol in an amount of 50 times by weight of the gel-like product in dry state was introduced into a flask provided with a stirrer and kept at a temperature of 0° to 5° C., and the above-mentioned frozen gel-like product was added to the solution to carry out a reaction for 5 hours. The reaction was further carried out at a temperature of 15° C. for 5 hours. After the reaction was over, the reaction mixture was filtered to obtain a solid material which was washed with ethanol and then was dispersed into distilled water, and was neutralized with an aqueous 1 N solution of hydrochloric acid while cooling from outside. The thus obtained solid material was separated by filtration and washed with water to obtain spherically shaped gel-like material.

It was found from the results of infrared absorption spectroscopy that the product had not been de-acetylated. The degree of cross-linking in the product was 0.10 per one pyranose ring.

EXAMPLE 5

The spherically shaped and cross-linked gel-like product prepared in Example 4 was sifted to be a size of 50 to 100 microns and filled into a column of 2 cm in inner diameter in a volume of 150 ml.

A specimen comprising a solution prepared by dissolving each 20 mg of blue-dextran, dextran of molecular weight of $10^4$, dextran of molecular weight of $10^5$ and dextran of molecular weight of $2.5 \times 10^5$ together into 2 ml of distilled water was poured into the above-mentioned column, and the content of the column was eluted with distilled water at a rate of 1 ml/min. The eluants were analyzed by a total carbon analyzer and an infrared analyzer. The elution-pattern thus obtained is shown in Table 1. As is clearly seen in Table 1, the gel-like material had a capability of separation to the substance of molecular weight of $2.5 \times 10^5$.

TABLE 1

| | Elution Pattern |
|---|---|
| Components of specimen | Amount of Eluant (ml) |
| Blue-dextran of mol. wt. of $2 \times 10^6$ | 55 to 65 |
| Dextran of mol. wt. of $2.5 \times 10^5$ | 75 to 85 |
| Dextran of mol. wt. of $1.0 \times 10^5$ | 100 to 110 |
| Dextran of mol. wt. of $1.0 \times 10^4$ | 120 to 130 |

EXAMPLE 6

A homogeneous solution was prepared by dissolving 5 g of de-N-acetylated product of glyceride-chitin (degree of substitution of 0.5 and degree of de-acetylation of 0.5) into 100 g of an aqueous 5% solution of acetic acid containing also 20 mg of blue-dextran of molecular weight of $2 \times 10^6$. Into the thus prepared solution, a liquid mixture prepared by adding 1 g of polyoxyethylene sorbitan monooleate as the surfactant and 5 g of benzene as the porosity-regulating agent into 100 g pyridine as the diluent was slowly added to make a homogeneous liquid, hereinafter refer to Liquid A.

On the other hand, in a flask provided with a stirrer, 2 liters of toluene, 50 ml of acetic anhydride and 10 g of polyoxyethylene sorbitan monooleate were introduced under agitation to be a homogeneous solution, and into the thus prepared solution, the above-mentioned Liquid A was added under agitation to carry out a reaction for 2 hours at room temperature under agitation of 1,000 rpm.

On carrying out the same procedures to the reaction mixture as in Example 1, a gel-like product light blue in colour was obtained consisting of minute spherically shaped particles of 50 to 200 microns in diameter under microscope, with clearly porous surface. The product did not dissolve both in acids and alkaline solutions, and the light blue colour of the product did not disappear when it was put into acids and alkalies. From this finding, it is considered that in the gel-like material, high molecular substance such as blue dextran is confined.

EXAMPLE 7

Except for using respectively 10 and 25 g of toluene instead of using 20 g of toluene as the porosity-regulating agent in the preparation of the emulsifying solution of Example 1, the same procedures were taken as in Example 1 to prepare two kinds of gel-like porous and shaped material.

Figure 2:
Figure 3:
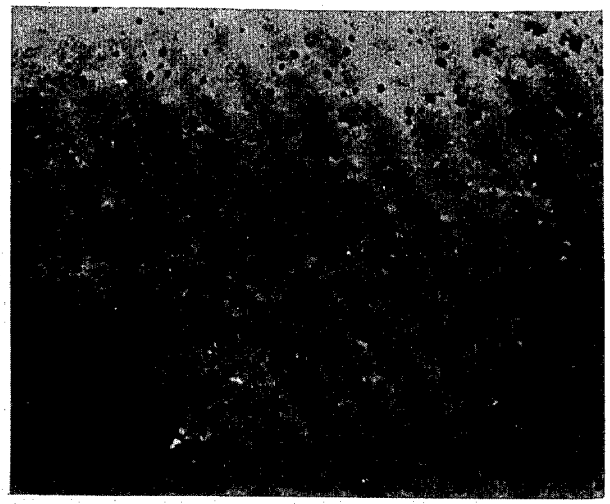
Figure 4:
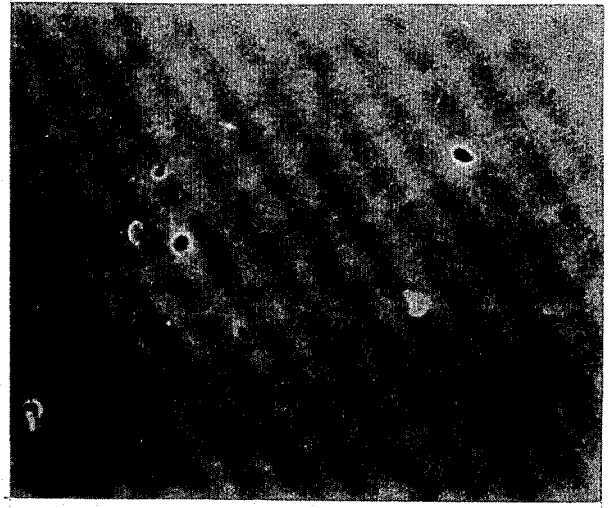

The states of the surface of the thus obtained porous and shaped materials are taken by a scanning electron microscopic photography and shown in FIGS. 1, 2 and 3. FIG. 1 shows a photograph magnified by 2,800 times when the amount of toluene used was 10 g, FIG. 2 shows the same, however, magnified by 1,400 times, and FIG. 3 shows a photograph magnified by 1,400 times of the product when 25 g of toluene was used. For the purpose of comparison, the state of surface of the spherically shaped material prepared by a method in Example 1 in which no toluene as the porosity-regulating agent was used is shown in FIG. 4.

It is added that these microphotographs of the images of scanning electron microscope were taken after substituting water of the gel-like material with isoamyl acetate and drying at its critical temperature.

As are clearly seen in FIGS. 1, 2 and 3, the poresize and its distribution in the shaped material can be regulated by optionally selecting the amount of porosity-regulating agent, toluene, in the aqueous solution of soluble derivative of chitin according to the invention.

What is claimed is:

1. A process for producing a porous shaped material of acylated chitin derivative comprising:
   (a) preparing an aqueous chitin solution containing 0.1 to 10% by weight of a solubilized derivative of chitin;
   (b) adding 0.1 to 5 parts by weight of a diluent, 0.001 to 1 part of a porosity-regulating agent, and 0.01 to 0.1 part by weight of a non-ionic surfactant to 1.0 part by weight of the aqueous solution; and
   (c) further adding the resultant liquid mixture of (a) and (b) to an acylating solution comprising:
      (i) an organic acid anhydride in an amount corresponding to 1 to 100 times by equivalent weight per 1 amino group of the solubilized group of chitin;
      (ii) an organic solvent in an amount equivalent to 10 to 1000 parts by weight of the organic acid anhydride; and
      (iii) a non-ionic surfactant in an amount equivalent to 0.01 to 0.1% by weight of acylating solution; at a temperature of 5° to 80° C. thereby bringing the acylating solution into reaction with the solubilized derivative of chitin.

2. A process according to claim 1, wherein said soluble derivative of chitin is a compound represented by the following general formula:

wherein R represents a carboxyalkyl group with two to four carbon atoms, a hydroxyethyl group, a hydroxypropyl group, a dihydroxypropyl group or an alkyl group with one to three carbon atoms; x is a number of 0.1 to 1.0; y=1.0−x, a is a number of 0 to 1.0 and b=1.0−a,
or a salt thereof.

3. A process according to claim 1, wherein said diluent is an alcohol with one to four carbon atoms, pyridine, an ether represented by the following general formula:

wherein R and R' respectively represent a hydrogen atom or an alkyl group with one to four carbon atoms
and n represents an integer of 1, 2, 3 or a mixture thereof.

4. A process according to claim 1, wherein said porosity-regulating agent is a volatile alkylbenzene.

5. A process according to claim 4, wherein said volatile alkylbenzene is benzene, toluene or xylene.

6. A process according to claim 1, wherein said organic acid anhydride is one or more kinds of aliphatic or aromatic organic acid anhydride with two to twenty carbon atoms.

7. A process according to claim 1, wherein said surfactant is monolaurate, monopalmitate, monostearate, monooleate or trioleate of sorbitan or of polyoxyethylene sorbitan.

8. A process according to claim 1, wherein said solution of said organic acid anhydride further contains an organic acid and an organic solvent selected from the group consisting of benzene, toluene and xylene.

9. A process according to claims 2, 3, 4, 5, 6, 7, 8, or 1 wherein the acylating product of the solubilized derivative of chitin is further cross-linked.

* * * * *